(12) United States Patent
Schneider et al.

(10) Patent No.: US 8,267,850 B2
(45) Date of Patent: Sep. 18, 2012

(54) TRANSCRANIAL MAGNET STIMULATION OF DEEP BRAIN TARGETS

(75) Inventors: M. Bret Schneider, Portola Valley, CA (US); David J. Mishelevich, Playa del Rey, CA (US)

(73) Assignee: Cervel Neurotech, Inc., Foster City, CA (US)

( * ) Notice: Subject to any disclaimer, the term of this patent is extended or adjusted under 35 U.S.C. 154(b) by 828 days.

(21) Appl. No.: 12/324,227

(22) Filed: Nov. 26, 2008

(65) Prior Publication Data
US 2009/0156884 A1 Jun. 18, 2009

Related U.S. Application Data

(60) Provisional application No. 60/990,300, filed on Nov. 27, 2007, provisional application No. 60/992,385, filed on Dec. 5, 2007.

(51) Int. Cl.
*A61N 2/02* (2006.01)
(52) U.S. Cl. ............................................. 600/14; 600/9
(58) Field of Classification Search ................. 600/9, 13, 600/14; 128/897–899
See application file for complete search history.

(56) References Cited

U.S. PATENT DOCUMENTS

| | | | |
|---|---|---|---|
| 4,134,395 A | 1/1979 | Davis | |
| 4,889,526 A | 12/1989 | Rauscher et al. | |
| 5,207,223 A | 5/1993 | Adler | |
| 5,267,938 A | 12/1993 | Konotchick | |
| 5,427,097 A | 6/1995 | Depp | |
| 5,441,495 A | 8/1995 | Liboff et al. | |
| 5,531,227 A | 7/1996 | Schneider | |
| 5,707,334 A | 1/1998 | Young | |
| 5,766,124 A | 6/1998 | Polson | |
| 5,891,034 A | 4/1999 | Bucholz | |
| 6,042,531 A | 3/2000 | Holcomb | |
| 6,132,361 A | 10/2000 | Epstein et al. | |
| 6,132,631 A | 10/2000 | Nallan et al. | |
| 6,179,770 B1 | 1/2001 | Mould | |
| 6,179,771 B1 | 1/2001 | Mueller | |
| 6,198,958 B1 | 3/2001 | Ives et al. | |
| 6,236,875 B1 | 5/2001 | Bucholz et al. | |
| 6,266,556 B1 | 7/2001 | Ives et al. | |

(Continued)

FOREIGN PATENT DOCUMENTS
DE 10242542 A1 4/2004
(Continued)

OTHER PUBLICATIONS

Hayward G, Goodwin GM, and Harmer CJ. The role of the anterior cingulate cortex in the counting Stroop task. Exp Brain REs (2004) 154: 355-358.*

(Continued)

*Primary Examiner* — Charles A Marmor, II
*Assistant Examiner* — Joshua D Lannu
(74) *Attorney, Agent, or Firm* — Shay Glenn LLP

(57) ABSTRACT

The treatment of specific neurological and psychiatric illnesses using Transcranial Magnetic Stimulation (TMS) requires that specific neuroanatomical structures are targeted using specific pulse parameters. Described herein are methods of positioning and powering TMS electromagnets to selectively stimulate a deep brain target region while minimizing the impact on non-target regions between the TMS electromagnet and the target. Use of these configurations may involve a combination of physical, spatial and/or temporal summation. Specific approaches to achieving temporal summation are detailed.

32 Claims, 7 Drawing Sheets

U.S. PATENT DOCUMENTS

| | | |
|---|---|---|
| 6,351,573 B1 | 2/2002 | Schneider |
| 6,356,781 B1 | 3/2002 | Lee et al. |
| 6,425,852 B1 | 7/2002 | Epstein et al. |
| 6,447,440 B1 | 9/2002 | Markoll |
| 6,461,289 B1 | 10/2002 | Muntermann |
| 6,488,617 B1 * | 12/2002 | Katz .............................. 600/26 |
| 6,537,197 B1 | 3/2003 | Ruohonen et al. |
| 6,571,123 B2 | 5/2003 | Ives et al. |
| 6,572,528 B2 | 6/2003 | Rohan et al. |
| 6,663,556 B2 | 12/2003 | Barker |
| 6,849,040 B2 | 2/2005 | Ruohonen et al. |
| 6,972,097 B2 | 12/2005 | Yoshida et al. |
| 7,087,008 B2 | 8/2006 | Fox et al. |
| 7,088,210 B2 | 8/2006 | Day et al. |
| 7,104,947 B2 | 9/2006 | Riehl |
| 7,153,256 B2 | 12/2006 | Riehl et al. |
| 7,236,830 B2 | 6/2007 | Gliner |
| 7,239,910 B2 | 7/2007 | Tanner |
| 7,367,936 B2 | 5/2008 | Myers et al. |
| 7,396,326 B2 | 7/2008 | Ghiron et al. |
| 7,483,747 B2 | 1/2009 | Gliner et al. |
| 7,520,848 B2 | 4/2009 | Schneider et al. |
| 7,771,341 B2 | 8/2010 | Rogers |
| 7,856,264 B2 | 12/2010 | Firlik et al. |
| 7,904,134 B2 | 3/2011 | McIntyre et al. |
| 8,052,591 B2 | 11/2011 | Mishelevich |
| 2002/0097125 A1 | 7/2002 | Davey |
| 2003/0004392 A1 | 1/2003 | Tanner et al. |
| 2003/0028072 A1 | 2/2003 | Fischell et al. |
| 2003/0065243 A1 | 4/2003 | Tanner |
| 2003/0204135 A1 | 10/2003 | Bystritsky |
| 2004/0010177 A1 | 1/2004 | Rohan et al. |
| 2004/0077921 A1 | 4/2004 | Becker et al. |
| 2004/0078056 A1 | 4/2004 | Zangen et al. |
| 2004/0193000 A1 | 9/2004 | Riehl |
| 2004/0193002 A1 | 9/2004 | Tanner et al. |
| 2005/0033154 A1 | 2/2005 | deCharms |
| 2005/0107655 A1 | 5/2005 | Holzner |
| 2005/0113630 A1 | 5/2005 | Fox et al. |
| 2005/0124848 A1 | 6/2005 | Holzner |
| 2005/0148808 A1 | 7/2005 | Cameron et al. |
| 2005/0154426 A1 | 7/2005 | Boveja et al. |
| 2005/0222625 A1 | 10/2005 | Laniado et al. |
| 2005/0234286 A1 | 10/2005 | Riehl et al. |
| 2005/0256539 A1 | 11/2005 | George et al. |
| 2006/0058853 A1 | 3/2006 | Bentwich |
| 2006/0094924 A1 | 5/2006 | Riehl et al. |
| 2006/0106430 A1 * | 5/2006 | Fowler et al. .................... 607/45 |
| 2006/0122454 A1 | 6/2006 | Riehl et al. |
| 2006/0122496 A1 | 6/2006 | George et al. |
| 2006/0149337 A1 | 7/2006 | John |
| 2006/0173274 A1 | 8/2006 | George et al. |
| 2006/0189866 A1 | 8/2006 | Thomas et al. |
| 2006/0218790 A1 | 10/2006 | Day et al. |
| 2006/0287566 A1 * | 12/2006 | Zangen et al. .................... 600/15 |
| 2007/0027353 A1 | 2/2007 | Ghiron et al. |
| 2007/0027504 A1 | 2/2007 | Barrett et al. |
| 2007/0100392 A1 | 5/2007 | Maschino et al. |
| 2007/0100398 A1 | 5/2007 | Sloan |
| 2007/0265489 A1 | 11/2007 | Fowler et al. |
| 2007/0293916 A1 | 12/2007 | Peterchev |
| 2008/0033297 A1 | 2/2008 | Sliwa |
| 2008/0058582 A1 | 3/2008 | Aho et al. |
| 2008/0064950 A1 | 3/2008 | Ruohonen et al. |
| 2008/0123922 A1 * | 5/2008 | Gielen et al. ................. 382/131 |
| 2008/0161636 A1 | 7/2008 | Hurme et al. |
| 2008/0306326 A1 | 12/2008 | Epstein |
| 2009/0018384 A1 | 1/2009 | Boyden et al. |
| 2009/0024021 A1 | 1/2009 | George et al. |
| 2009/0099405 A1 | 4/2009 | Schneider et al. |
| 2009/0099623 A1 | 4/2009 | Bentwich |
| 2009/0112133 A1 | 4/2009 | Deisseroth et al. |
| 2009/0112277 A1 | 4/2009 | Wingeier et al. |
| 2009/0114849 A1 | 5/2009 | Schneider et al. |
| 2009/0124848 A1 | 5/2009 | Miazga |
| 2009/0187062 A1 | 7/2009 | Saitoh |
| 2009/0189470 A1 | 7/2009 | McClellan |
| 2009/0227830 A1 | 9/2009 | Pillutla et al. |
| 2010/0004500 A1 | 1/2010 | Gliner et al. |
| 2011/0082326 A1 | 4/2011 | Mishelevich et al. |
| 2011/0273251 A1 | 11/2011 | Mishelevich et al. |
| 2012/0016177 A1 | 1/2012 | Mishelevich et al. |

FOREIGN PATENT DOCUMENTS

| | | |
|---|---|---|
| EP | 0501048 A1 | 9/1992 |
| EP | 0709115 A1 | 5/1996 |
| EP | 0788813 A1 | 8/1997 |
| EP | 1326681 B1 | 1/2007 |
| GB | 2271931 A | 5/1994 |
| GB | 2336544 A | 10/1999 |
| KR | 10-0457104 | 11/2004 |
| WO | WO 98/56302 A1 | 12/1998 |
| WO | WO 99/39769 A1 | 8/1999 |
| WO | WO 99/55421 A2 | 11/1999 |
| WO | WO 00/74777 A1 | 12/2000 |
| WO | WO 00/78267 A2 | 12/2000 |
| WO | WO 02/09811 A1 | 2/2002 |
| WO | WO 02/32504 A2 | 4/2002 |
| WO | WO 2003/082405 A1 | 10/2003 |
| WO | WO 2004/087255 A1 | 10/2004 |
| WO | WO 2005/000153 A2 | 1/2005 |
| WO | WO 2006/124914 A2 | 11/2006 |
| WO | WO 2007/050592 A2 | 5/2007 |
| WO | WO 2007/130308 A2 | 11/2007 |

OTHER PUBLICATIONS

Schneider et al.; U.S. Appl. No. 12/402,404 entitled "Robotic apparatus for targeting and producing deep, focused transcranial magnetic stimulation," filed Mar. 11, 2009.

Nadeem et al.; Computation of electric and magnetic stimulation in human head using the 3-D impedance method; IEEE Trans on Biomedical Eng; vol. 50; No. 7; pp. 900-907; Jul. 2003.

Sekino et al.; Comparison of current distributions in electroconvulsive therapy and transcranial magnetic stimulation; J. of Applied Physics; vol. 91; No. 10; pp. 8730-8732; May 15, 2002.

Schneider et al.; U.S. Appl. No. 12/838,299 entitled "Transcranial magnetic stimulation field shaping," filed Jul. 16, 2010.

Schneider et al.; U.S. Appl. No. 12/912,650 entitled "Sub-motor-threshold stimulation of deep brain targets using transcranial magnetic stimulation," filed Oct. 26, 2010.

Partsch et al.; U.S. Appl. No. 12/669,882 entitled "Device and method for treating hypertension via non-invasive neuromodulation," filed Jan. 20, 2010.

Schneider et al.; U.S. Appl. No. 12/671,260 entitled "Gantry and switches for position-based triggering of tms pulses in moving coils," filed Jan. 29, 2010.

Mishelevich et al.; U.S. Appl. No. 12/670,938 entitled "Firing patterns for deep brain transcranial magnetic stimulation," filed Jan. 27, 2010.

Schneider et al.; U.S. Appl. No. 12/701,395 entitled "Control and coordination of transcranial magnetic stimulation electromagnets for modulation of deep brain targets," filed Feb. 5, 2010.

Mishelevich et al.; U.S. Appl. No. 12/677,220 entitled "Focused magnetic fields," filed Mar. 9, 2010.

Mishelevich et al.; U.S. Appl. No. 12/679,960 entitled "Display of modeled magnetic fields," filed Mar. 25, 2010.

Mishelevich et al.; U.S. Appl. No. 12/680,749 entitled "Intra-session control of transcranial magnetic stimulation," filed Mar. 30, 2010.

Mishelevich et al.; U.S. Appl. No. 12/680,912 "Transcranial magnetic stimulation with protection of magnet-adjacent structures," filed Mar. 31, 2010.

Magstim Website: http://www.magstim.com/magneticstimulators/magstimacc/12494.html (printed Mar. 23, 2010).

Mayberg et al.; Deep brain stimulation for treatment-resistant depression; Neuron; vol. 45; pp. 651-660; 2005.

Agnew et al.; Considerations for safety in the use of extracranial stimulation for motor evoked potentials; Neurosurgery; vol. 20; pp. 143-147; Jan. 1987.

Avery et al.; A Controlled Study of Repetitive Transcranial Magnetic Stimulation in Medication-Resistant Major Depression; Biological Psychiatry; vol. 59; pp. 187-194; Jul. 2005.

Barker et al.; Non invasive magnetic stimulation of the human motor cortex; Lancet; vol. 1; pp. 1106-1110; May 1985.

Barker, A. T.; An introduction to the basic principles of magnetic nerve stimulation; Journal of Clinical Neurophysiology; vol. 8; No. 1; pp. 26-37; Jan. 1991.

Basser et al.; Stimulation of myelinated nerve axon by electromagnetic induction; Medical & Biological Engineering and Computing.; vol. 29; pp. 261-268; May 1991.

Bohning et al.; Mapping transcranial magnetic stimulation (TMS) fields in vivo with MRI; NeuroReport; vol. 8; No. 11; pp. 2535-2538; Jul. 28, 1997.

Conca et al.; Effect of chronic repetitive transcranial magnetic stimulation on regional cerebral blood flow and regional cerebral glucose uptake in drug treatment-resistant depressives. A brief report; Neuropsychobiology; vol. 45; No. 1; pp. 27-31; (Month Unavailable) 2002.

Dantec magnetic stimulation product information on MagPro X100 with MagOption; http://www.danica.nl/neuro/neuro-magnetische-stimulatoren.htm; Jan. 15, 2009.

Davey et al.; Designing transcranial magnetic stimulation systems; IEEE Transactions on Magnetics; vol. 41; No. 3; pp. 1142-1148; Mar. 2005.

Davey et al.; Modeling the effects of electrical conductivity of the head on the induced electrical field in the brain during magnetic stimulation; Clinical Neurophysiology; vol. 114; pp. 2204-2209; Jun. 2003.

Davey et al.; Prediction of magnetically induced electric fields in biologic tissue; IEEE Transactions on Biomedical Engineering; vol. 38; pp. 418-422; May 1991.

Davey et al.; Suppressing the surface field during transcranial magnetic stimulation; IEEE Transactions on Biomedical Engineering; vol. 53; No. 2; Feb. 2006; pp. 190-194.

DeRidder et al.; Transcranial magnetic stimulation for tinnitus: influence of tinnitus duration on stimulation parameter choice and maximal tinnitus suppression; Otol Neurotol.; vol. 26; No. 4; pp. 616-619; Jul. 2005.

Epstein et al.; Magnetic coil suppression of visual perception at an extracalcarine site; J. Clin. Neurophysiol; vol. 13; No. 3; pp. 247-252; May 1996.

George, Mark S.; Stimulating the brain; Scientific American; Sep. 2002; pp. 67-73.

Han et al.; Multichannel magnetic stimulation system design considering mutual couplings among the stimulation coils; IEEE Trans. on Biomedical Engineering; vol. 51; No. 5; pp. 812-817; May 2004.

Hemond et al.; Transcranial magnetic stimulation in neurology: What we have learned from randomized controlled studies; Neuromodulation: Technology at the Neural Interface; vol. 10; No. 4; pp. 333-344; 2007.

Hovey, C. et al.; The new guide to magnetic stimulation; The Magstim Company Ltd.; Carmarthenshire, United Kingdom; Oct. 2003.

Huang et al.; Theta Burst Stimulation of the Human Motor Cortex; Neuron; vol. 45; pp. 201-206; Jan. 2005.

Isenberg et al.; Low frequency rTMS stimulation of the right frontal cortex is as effective as high frequency rTMS stimulation of the left frontal cortex for antidepressant-free, treatment-resistant depressed patients; Ann Clin Psychiatry; vol. 17; No. 3; pp. 153-159; Jul.-Sep. 2005.

Lang et al.; How does transcranial Dc stimulation of the primary motor cortex alter regional neuronal activity in the human brain?; Eur. J. Neurosci.; vol. 22; No. 2; pp. 495-504; Jul. 2005.

Lin et al.; Magnetic coil design considerations for functional magnetic stimulation; IEEE Trans. on Biomedical Eng.; vol. 47; No. 5; pp. 600-610; May 2000.

Martin et al.; Transcranial magnetic stimulation for treating depression; Cochrane Review; (Month Unavailable) 2002 (in (eds.): The Cochrane Library. Oxford: Update Software: The Cochrane Library. Oxford: Update Software.).

Ohnishi et al.; rCBF changes elicited by rTMS over DLPFC in humans; Suppl Clin Neurophysiol.; vol. 57: pp. 715-720; (Month Unavailable) 2004.

Paton et al.; Vascular-brain signaling in hypertension: role of angiotensin II and nitric oxide; Curr. Hypertens Rep; vol. 9; No. 3; pp. 242-247; Jun. 2007.

Roth et al.; A coil design for transcranial magnetic stimulation of adeep brain regions; J. Clin. Neurophysiology; vol. 19; No. 4; Aug. 2002; pp. 361-370.

Ruohonen et al.; Theory of Multichannel Magnetic Stimulation: Toward Functional Neuromuscular Rehabilitation; IEEE Transactions on Biomedical Engineering; vol. 46; No. 6; pp. 646-651; Jun. 1999.

Ruohonen, J.; Transcranial magnetic stimulation: modelling and new techniques; (doctoral dissertation); Helsinki Univ. of Tech.; Dept. of Eng. Physics and Mathematics; Espoo, Finland; Dec. 1998.

Ruohonen et al.; (Chapter 2); Magnetic stimulation in clinical neurophysiology; Second Ed.; Ed. Elsevier Inc.; pp. 17-30; (Month Unavailable) 2005.

Ruohonen et al.; Focusing and targeting of magnetic brain stimulation using multiple coils; Medical & Biological Engineering and Computing; vol. 35; pp. 297-301; May 1998.

Sackheim, H. A.; Commentary: Magnetic stimulation therapy and ECT; Convulsive Therapy; vol. 10; No. 4; Dec. 1994; pp. 255-285.

Speer et al.; Opposite effects of high and low frequency rTMS on regional brain activity in depressed patients; Biol. Psychiatry; vol. 48; No. 12; pp. 1133-1141; Dec. 15, 2000.

Takano et al.; Short-term modulation of regional excitability and blood flow in human motor cortex following rapid-rate transcranial magnetic stimulation; Neuroimage; vol. 23; No. 3; pp. 849-859; Nov. 2004.

Traad, Monique; A Quantitative Positioning Device for Transcranial Magnetic Stimulation; Engineering in Medicine and Biology Society; 1990; Proceedings of the 12th Annual Int'l Conf. of the IEEE; Philadelphia, PA; p. 2246; Nov. 1-4, 1990.

Ueno et al.; Localized stimulation of neural tissues in the brain by means of a paired configuration of time-varying magnetic fields; J. Appl. Phys.; vol. 64; No. 10; pp. 5862-5864; Nov. 15, 1988.

Vayssettes-Courchay et al.; Role of the nucleus tractus solitarii and the rostral depressive area in the sympatholytic effect of 8-hydroxy-2-(di-n-propylamino)tetralin in the cat; Eur. J. Pharmacol.; vol. 242; No. 1; pp. 37-45; Sep. 21, 1993.

Wagner et al.; Three-dimensional head model simulation of transcranial magnetic stimulation; IEEE Trans. on Biomedical Engineering; vol. 51; No. 9; pp. 1586-1598; Sep. 2004.

Waki et al.; Junctional adhesion molecule-1 is unregulated in spontaneously hypertensive rats: evidence for a prohypertensive role within the brain stem; Hypertension; vol. 49; No. 6; pp. 1321-1327; Jun. 2007.

Wasserman et al.; Therapeutic application of repetitive magnetic stimulation: a review; Clinical Neurophysiology; vol. 112; pp. 1367-1377; Apr. 2001.

Wasserman, E. M.; Risk and safety of repetitive transcranial magnetic stimulation: report and suggested guidelines from the International Workshop on the Safety of Repetitive Transcranial Magnetic Stimulation, Jun. 5-7, 1996; Electro-encephalography and Clinical Neurophysiology; vol. 108; pp. 1-16; Jan. 1998.

Xiao et al.; Magnetic Nanocomposite Paste: An Ideal High-μ, k and Q Nanomaterial for Embedded Inductors in High Frequency Electronic Appls.; Proceedings of the 9th World Multiconference on Systemics, Cybernetics and Informatics; Orlando, FL; Jul. 10-13, 2005.

Mishelevich et al.; U.S. Appl. No. 12/990,235 entitled "Transcranial magnetic stimulation by enhanced magnetic field perturbations," filed Oct. 29, 2010.

Schneider, M. Bret .; U.S. Appl. No. 13/169,967 entitled "Enhanced Spatial Summation for Deep-Brain Transcranial Magnetic Stimulation," filed Jun. 27, 2011.

Hsu et al., Analysis of Efficiency of Magnetic Stimulation; IEEE Transactions on Biomedical Engineering; vol. 50. No. 11; Sep. 2003; pp. 1276-1285.

Kamitani et al.; A model of magnetic stimulation of neocortical neurons; Neurocomputing; vol. 38; No. 40; Jun. 2001; pp. 697-703.

Miranda et al.; The Electric Field Induced in the Brain by Magnetic Stimulation: A 3-D Finite-Element Analysis of the Effects of Tissue Heterogeneity and Anisotropy; IEEE Transactions on Biomedical Engineering; vol. 50; No. 9; Sep. 2003; pp. 1074-1085.

Wagner et al.; Transcranial direct current stimulation: A computer-based human model study; NeuroImage; vol. 35; issue 3; Apr. 15, 2007; pp. 1113-1124.

Yang et al.; 3D Realistic Head Model Simulation Based on Transcranial Magnetic Stimulation; Conf Proc IEEE Eng Med Biol Soc.; vol. Suppl.; Aug. 30-Sep. 3, 2006; 4 pages.

* cited by examiner

| Coil/Trajectory Number | Shown in Diagram As: | Power at Cortical Sulcus (%MT) | Distance from Cortical Sulcus to Cingulate Target (cm) | Calculated Power Reaching Target (%MT) |
|---|---|---|---|---|
| 1 | Blue (Left) | 99% | 1.5 | 33% |
| 2 | Blue (Right) | 99% | 1.5 | 33% |
| 5 | Dk Green (Anterior) | 99% | 1 | 50% |
| | | | | |
| Total Power Reaching Target | | | | 116% |

FIG. 5E

| Coil/Trajectory Number | Shown in Diagram As: | Power at Cortical Surface (%MT) | Distance from Cortical Surface to Cingulate Target (cm) | Calculated Power Reaching Target (%MT) |
|---|---|---|---|---|
| 1 | Red (Left) | 99% | 1.98 | 25% |
| 2 | Red (Right) | 99% | 1.98 | 25% |
| 3 | Blue (Left) | 99% | 3.39 | 15% |
| 4 | Blue (Right) | 99% | 3.39 | 15% |
| 5 | Green (Anterior) | 99% | 2.35 | 21% |
| 6 | Yellow (Posterior) | 99% | 4.36 | 11% |
| Total Power Reaching Target | | | | 112% |

FIG. 6E

TRANSCRANIAL MAGNET STIMULATION OF DEEP BRAIN TARGETS

CROSS REFERENCE TO RELATED APPLICATIONS

This application claims priority to the following applications: U.S. Provisional Patent Application Ser. No. 60/990,300, filed on Nov. 27, 2007, titled "TARGET-SPECIFIC COIL CONFIGURATIONS FOR TRANSCRANIAL MAGNETIC STIMULATION" and U.S. Provisional Patent Application Ser. No. 60/992,385, filed on Dec. 5, 2007, titled "CINGULATE TMS COIL CONFIGURATIONS WITH TEMPORAL SUMMATION." These applications are herein incorporated by reference in its entirety.

INCORPORATION BY REFERENCE

All publications and patent applications mentioned in this specification are herein incorporated by reference in their entirety to the same extent as if each individual publication or patent application was specifically and individually indicated to be incorporated by reference.

FIELD OF THE INVENTION

The devices and methods described herein relate generally to the field of Transcranial Magnetic Stimulation.

BACKGROUND OF THE INVENTION

Transcranial Magnetic Stimulation (TMS) has been employed to treat neurological and psychiatric illnesses, including depression refractory to the administration of drugs. The number of treatable conditions may significantly increase as the depth of the target increases. Systems for targeting neural structures at depth (e.g., Schneider and Mishelevich, U.S. patent application Ser. No. 10/821,807, and Mishelevich and Schneider, U.S. patent application Ser. No. 11/429,504) may include multiple electromagnets, the firing of which must be coordinated. TMS stimulation of deep targets would potentially permit treatment of a variety of conditions such as chronic pain, addiction, obesity, depression, Alzheimer's disease, and Parkinson's disease. Conventional rTMS (repetitive Transcranial Magnetic Stimulation) is capable of effectively stimulating only the outer cortical layer of the brain, and treats depression indirectly, by stimulating neural pathways that run from the prefrontal cortical surface to the cingulate gyrus, rather than hitting the target directly. It is preferable to stimulate deep structures such as the cingulate gyrus directly, but when targeting deep neural structures with rTMS, care must be taken to avoid overstimulating superficial structures to eliminate undesired side effects such as seizures or producing unintended neural-stimulation results. It is thus necessary to avoid having successive pulses from the same electromagnet passing through such superficial structures while targeting the deep structure, particularly when the strength of the magnetic field (e.g., the field intensity) is sufficient to activate or depolarize non-target tissues between the TMS electromagnet and the deep brain target.

To effectively elicit an action potential in a neural structure such as a deep brain target, adequate stimulation must be received in a time period that is less than the minimum time (usually expressed as chronaxie) that it takes the target neural membrane to re-polarize. Otherwise threshold for generating an action potential will not be achieved. With respect to another time scale, for a given neural structure, stimulating pulses must be received within a maximum effective time interval such that the effect of the generated action potentials is additive. Neural elements are typically highly interconnected and the actual final target element to be stimulated will receive inputs from multiple sources.

Typical deep brain target regions may include, for example, the insula and the cingulate gyrus. Stimulation of a target deep brain regions without stimulating or depressing stimulation of nearby non-target brain region, and particularly brain regions between the target deep brain region and the TMS electromagnet, may be achieved by optimizing the power applied to the TMS electromagnet(s) so that the electromagnetic field(s) reaching the target sum to achieve the desired stimulation. Optimization typically means minimizing the power applied (and/or the rate power is applied) to a TMS electromagnet so that the intervening non-target regions are not stimulated.

Thus, power applied to any given electromagnet, and/or the rate that the power is applied, is preferably limited. However, the power applied by one or more TMS electromagnets intended to stimulate a deep brain target such as the insula or cingulate gyrus must be sufficient to activate the deep brain target. While limiting the power and frequency from a single stimulating location may protect structures superficial to the deeper target, it may be impossible to effectively stimulate a deep target because of the rapid fall off of the magnetic field. The attenuation of the magnetic field is commonly believed to be equivalent to roughly $1/(distance)^2$ at short distances. This inverse-square relationship is particularly significant, and a version of this relationship has been used to determine the strength needed for stimulation of a deep brain target region by one or more TMS electromagnets.

Known deep-brain stimulation techniques, including those described by Mishelevich and Schneider described above, have generally applied the inverse-square relationship to determine the stimulation power and/or frequency to be applied. Described herein are methods of more accurately estimating the applied power necessary from one or more TMS electromagnets to prevent or minimize stimulation of intervening non-target regions. In particular, the methods described herein may be used to determine the power (e.g., minimum power) necessary to stimulate a deep brain region target. This may allow the stimulation to be kept below the motor threshold (MT) for stimulation, to avoid stimulation of the intervening non-target region.

In general, the treatment of specific neurological and psychiatric illnesses using rTMS requires that specific neuroanatomical structures be targeted using specific pulse parameters. This may be greatly facilitated by using magnetic coils placed in specific positions with respect to one another, and with respect to the neuroanatomical target. Proper coil configuration ensures that neuromodulation of the targeted structure is optimally accomplished, with minimal perturbation of neural tissue between the electromagnet coils and the target, including nearby areas outside of the target region. Described herein are methods and systems for the optimal placement of TMS coils and coil arrays relative to the human head, specific geometries, and specific brain targets, as well as method and systems for determining the optimal power and/or frequency applied to stimulate the target without stimulating non-target regions.

This application hereby incorporates by reference in their entirety the following co-pending patent applications: "DEVICE AND METHOD FOR TREATING HYPERTENSION VIA NON-INVASIVE NEUROMODULATION" (PCT/US2008/071663), filed Jul. 30, 2008; "GANTRY AND SWITCHES FOR POSITION-BASED TRIGGERING OF TMS PULSES IN MOVING COILS" (PCT/US2008/072930), filed Aug. 12, 2008; "FIRING PATTERNS FOR DEEP BRAIN TRANSCRANIAL MAGNETIC STIMULATION" (PCT/US2008/073751), filed Aug. 20, 2008; "FOCUSING MAGNETIC FIELDS WITH ATTRACTOR MAGNETS AND CONCENTRATOR DEVICES" (PCT/US2008/075575) filed Sep. 8, 2008; "PITCH, ROLL, AND YAW MOTIONS FOR ELECTROMAGNET ARRAYS" (PCT/US2008/075583), filed Sep. 8, 2008; "FOCUSED MAGNETIC FIELDS" (PCT/US2008/075706), filed Sep. 9, 2008; "AUTOMATED MOVEMENT OF ELECTROMAGNETS TRACKING ECCENTRICITY OF THE HEAD" (PCT/US2008/075824), filed Sep. 10, 2008; "SYSTEMS AND METHODS FOR COOLING ELECTROMAGNETS FOR TRANSCRANIAL MAGNETIC STIMULATION" (PCT/US2008/077851), filed Sep. 26, 2008; "DISPLAY OF MODELED MAGNETIC FIELDS" (PCT/US2008/079378), filed Oct. 9, 2008; "INTRA-SESSION CONTROL OF TRANSCRANIAL MAGNETIC STIMULATION" (PCT/US2008/081048), filed Oct. 24, 2008; "TRANSCRANIAL MAGNETIC STIMULATION WITH PROTECTION OF MAGNET-ADJACENT STRUCTURES" (PCT/US2008/081307), filed Oct. 27, 2008; and "MONOPHASIC MULTI-COIL ARRAYS FOR TRANSCRANIAL MAGNETIC STIMULATION" (U.S. patent application Ser. No. 12/185,544), filed Aug. 4, 2008.

SUMMARY OF THE INVENTION

Described herein are methods and systems for stimulating target deep brain regions using one or more Transcranial Magnetic Stimulation (TMS) electromagnets. These methods may include the step of optimizing the stimulation protocol and/or the position/orientation of the TMS electromagnet by stimulating one or more sulci near or adjacent to the target deep brain target region. In particular, the methods described herein may stimulate one or more sulci within a patient's brain so that the sulci can conduct the stimulation to the desired deep brain target region.

Also described herein are methods of stimulating a patient's cingulate gyrus specifically, and methods of stimulating a patient's insula specifically. For example, the methods and systems described herein may include the use of multiple magnetic coils, each pulsed serially in rapid succession, or simultaneously, followed by a longer interval before the pattern is repeated. This approach may allow impact on the activity of specific brain regions such as the dorsal anterior cingulate gyrus and associated fiber bundles and the insula. Modulating the activity of these brain regions enables the treatment of specific illnesses.

Described herein are Transcranial Magnetic Stimulation (TMS) methods for stimulating a brain region deep within a patient's brain, the method comprising the steps of positioning a first TMS electromagnet outside of a patient's head; determining the distance between a target deep brain region and a sulcus wherein the sulcus is within the range of a magnetic field emitted by the first TMS electromagnet; determining stimulation parameters for the first TMS electromagnet based on the distance between the target brain region and the sulcus; and applying energy to the first TMS electromagnet at the determined stimulation parameters.

The step of positioning may include aiming the TMS electromagnet at the sulcus, wherein the sulcus is adjacent to the target deep brain region. For example, the TMS electromagnet may stimulate the sulcus to cause the electrically conductive fluid within the sulcus to transmit a current towards the deep brain target that may help depolarize the deep brain target.

In some variations, the step of positioning may comprise aiming the TMS electromagnet at the target deep brain region. When multiple TMS electromagnets are used, as described more fully below, one or more of the TMS electromagnets may be directed to a sulcus, and one or more may be aimed at the deep brain target.

The step of determining the distance may also include the step of determining the distance between the target deep brain region and a portion of the sulcus closest to the target deep brain region.

In some variations, the method may also include the step of determining the direction of the pathway through the sulcus to the target deep brain region, wherein the step of determining the stimulation parameters comprises determining the stimulation parameters based on the direction of the pathway through the sulcus to the target deep brain region. For example, when stimulation from the TMS electromagnet is applied to the sulcus, the orientation of the stimulation applied may affect the stimulation of the deep brain region, based on the orientation of the current pathway through the sulcus.

For example, the step of determining the direction of the pathway through the sulcus may include determining an angle between the pathway through the sulcus and the target deep brain region. The method may also include aligning the TMS electromagnet based on the direction of the pathway through the sulcus and the angle between the pathway through the sulcus and the target deep brain region. Aligning the TMS electromagnet based on the orientation of the sulcus may help propagate the current through the sulcus to the desired deep brain target. Orienting the TMS electromagnet relative to the deep brain target may also help orient the current applied to the deep brain target.

The step of determining the stimulation parameters may include determining the duration, rate and power for the first TMS electromagnet. For example, the step of determining the stimulation parameters may include estimating the power achieved at the target based on estimating the attenuation of the applied power using the distance from the target deep brain region and the sulcus. This procedure may assume minimal loss of power through the sulcus, since the sulcus typically includes conductive fluid, so that the inverse-square assumption of loss does not strictly hold.

In any of these variations describe herein, a plurality of TMS electromagnets may be used to stimulate a deep brain target. For example, the method may include the step of positioning a second TMS electromagnet outside of the patient's head, and determining stimulation parameters for the second TMS electromagnet based on the distance between the target brain region and a sulcus that is within the range of a magnetic field emitted by the second TMS electromagnet. Any number of additional TMS electromagnets may be used (e.g., 2, 3, 4, 5, 6, or more). The method may also include the step of determining the direction of the pathway to the target deep brain region through the sulcus that is within the range of a magnetic field emitted by the second TMS electromagnet, wherein the step of determining the stimulation parameters for the second TMS electromagnet comprises determining the stimulation parameters based on the direction of the pathway to the target deep brain region through the sulcus that is within the range of a magnetic field emitted by the second TMS electromagnet.

The step of determining the direction of the pathway to the target deep brain region through the sulcus that is within the range of a magnetic field emitted by the second TMS electromagnet may include determining and angle between the pathway through the sulcus that is within range of the magnetic field emitted by the second TMS electromagnet and the target deep brain region.

In some variations, the method also includes aligning the second TMS electromagnet based on the direction of the pathway through the sulcus that is within the range of a magnetic field emitted by the second TMS electromagnet and the angle between the pathway through the target deep brain region and the sulcus that is within the range of a magnetic field emitted by the second TMS electromagnet.

In general, the step of determining the stimulation parameters may include limiting the power for each TMS electromagnet to be below the motor threshold (MT) at the cortical surface.

Also described herein are methods of TMS for stimulating a brain region deep within a patient's brain, the method including the steps of: positioning a plurality of TMS electromagnets outside of a patient's head; determining stimulation parameters for each TMS electromagnet based on the distance between a target deep brain region and a sulcus that is in the range of a magnetic field emitted by each TMS electromagnet; and applying energy to each of the plurality of TMS electromagnets at the determined stimulation parameters.

Any of the steps described above may be included as part of this method. For example, the step of determining the stimulation parameters may include limiting the power for each TMS electromagnet to be below the motor threshold at the cortical surface.

Methods of stimulating a specific brain region are also described herein, and may be used with any of the steps described above. For example, described herein are TMS methods for stimulating the cingulate region of a patient's brain while leaving the outer cortex relatively undisturbed. These methods may include the steps of: aiming a plurality of independently powerable TMS electromagnets at the cingulate region tracts of the patient's brain; determining stimulation parameters for each TMS electromagnet so that the power of the field emitted by each TMS electromagnet at the cortical surface is below the motor threshold; and triggering pulses from the TMS electromagnets at phase-complementary angles, wherein pulses from two or more TMS electromagnets are triggered within the membrane time constant of the target cingulate region.

The step of aiming may include aiming the plurality of independently powerable TMS electromagnets at tracts of the cingulate region. The step of aiming may comprise aiming the plurality of independently powerable TMS electromagnets at tracts of the patient's anterior cingulate.

In some variations, the step of aiming may comprise orienting each of the TMS electromagnets to stimulate the tracts of the cingulate region horizontally. Alternatively, the step of aiming may comprise orienting each of the TMS electromagnets to stimulate the tracts of the cingulate region transversely.

The step of aiming may comprise aiming a plurality of independently powerable V-shaped TMS electromagnets. The step of triggering pulses may comprise simultaneously triggering pulses from the two or more TMS electromagnets. The step of triggering pulses may further comprise triggering pulses from two or more TMS electromagnets within about 300 μs.

Also described herein are TMS methods for stimulating the insula region of a patient's brain while leaving the outer cortex relatively undisturbed. The method may include the steps of: positioning a plurality of independently powerable TMS electromagnets outside of the patient's head; aiming the plurality of independently powerable TMS electromagnets at the insula region of the patient's brain; determining stimulation parameters for each TMS electromagnet so that the power of the field emitted by each TMS electromagnet at the cortical surface is below the motor threshold; and triggering pulses from the TMS electromagnets at phase-complementary angles, wherein pulses from two or more TMS electromagnets are triggered within the membrane time constant of the target insula region.

In some variations, the method also includes the step of shielding the plurality of independently powerable TMS electromagnets to prevent mutual inductance; for example, shielding with a high-permeability mu-metal.

The step of aiming may include aiming a plurality of independently powerable V-shaped TMS electromagnets. The step of triggering pulses may include simultaneously triggering pulses from the two or more TMS electromagnets. In some variations, the method further comprises moving one or more of the TMS electromagnets and triggering additional pulses from the TMS electromagnets.

BRIEF DESCRIPTION OF THE DRAWINGS

FIGS. 6A-6D and 6E illustrate a second stimulation scenario, in which the falloff calculation is based on distance from gyral crown to target, requiring 5 to 6 trajectories.

DETAILED DESCRIPTION OF THE INVENTION

Figures 1A, 1B:
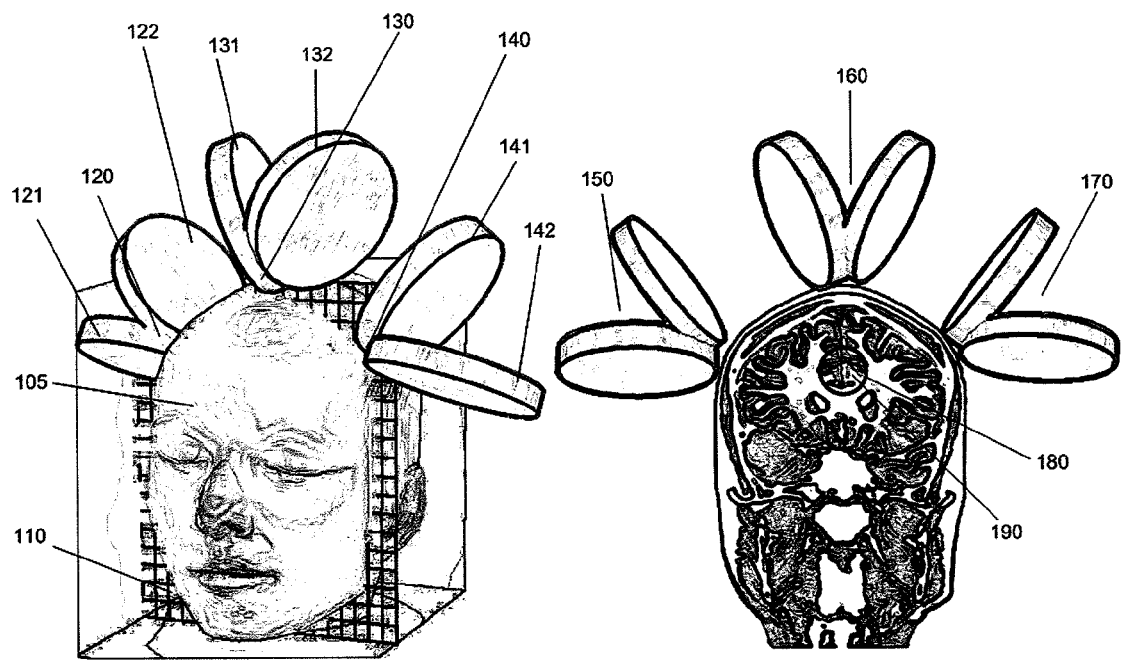
FIGS. 1A and 1B show perspective and partial cross-sectional views, respectively, of an array of three (v-shaped) double coils in a configuration designed to stimulate the dorsal cingulate fiber bundles, while leaving the outer cortex relatively undisturbed.

In general, the methods of Transcranial Magnetic Stimulation (TMS) described herein may be used to stimulate a deep brain region. In particular, these methods may be applied to specifically stimulate a deep brain region such as the cingulate gyrus or the insula. The method for stimulating these deep brain regions may include the steps of initially positioning one, or more typically a plurality of, TMS electromagnets around the patient's head. The plurality of TMS electromagnets may be directed at the desired deep brain target (e.g., insula or cingulate region). Alternatively, as described in greater detail below, the TMS electromagnets may be directed to a sulcus that is adjacent to the deep brain target. For example, the sulcus may be electrically continuous or connected to the deep target. Thus, any of the methods described herein may be performed in conjunction with brain imaging showing the location of the target region, as well as the configuration of any nearby sulci.

Sulci are typically grooves or fissures formed along the cerebral cortex of the brain. As used herein, a sulcus may be any fissure or channel within the brain. In general, the sulci are channels that are typically bathed in cerebrospinal fluid (CSF). CSF, in the non-pathological case, is a fluid having a high ionic content, and may therefore have a relatively high conductance. The methods described herein may take advantage of the electrical properties of the CSF by applying a magnetic field from a TMS electromagnet that evokes an electrical current in the CSF which may depolarize a target brain region. The intensity, location and direction of the evoked current may be selected in order to optimize stimulation of the target brain region. Sulci may be of different widths, orientations and lengths. For example, a sulcus may be shallow or superficial, and may extend only slightly from the cortical surface, or they may be deeper. A deep sulcus may extend relatively deeply into the brain, towards a deep brain target. Thus, a deep sulcus may be used as a pathway or conduit for stimulation of the deep brain structures as described herein.

Any appropriate brain scanning or imaging may be used. The imaging may be preformed prior to (or after) the positioning of the TMS electromagnets. Thus one or more fiducial markers may be used to help coordinate or transition between images taken and the TMS systems used herein. Although there are common neuroanatomical landmarks in between patients, there is considerable variation in the actual arrangement, size and position of such landmarks. For example, the position and extend of different (and particularly "minor") sulci may vary considerably. Thus, it may be beneficial to determine the location and orientation of any sulci adjacent to the target deep brain region. In particular, it may be beneficial to determine the extent that any such sulci extend in the direction from the target deep brain region and the outer surface of the head, where the TMS electromagnets are to be positioned. In addition, the orientation of such sulci relative to the target (e.g., parallel or transverse to the target or target fiber bundles).

Once the position and orientation of the target has been determined (e.g., by MRI or any other appropriate imaging modality), the TMS electromagnet may be positioned relative to the target and/or to a sulcus adjacent to the target. Thus, the TMS electromagnet may be "focused" so that the energy will be applied to the target region of the brain. In some variations, this may involve positioning the TMS electromagnet so that the emitted magnetic field is focused on the deep brain target region or on a region (e.g., sulci, or fibers) that is electrically connected to the target brain region. Any appropriate deep brain target region may be selected. In general a deep brain target region is a one that is not a superficial (e.g., cortical) brain region, within relatively close proximity to the patient's skull. Targeting of such deep brain regions is a distinction from most routinely performed TMS, which is limited to stimulation of only relatively superficial regions of the brain.

A plurality of TMS electromagnets may be positioned or focused on the target brain region and/or on sulci or other regions that are electrically connected to the target deep brain region. Focusing may include selecting both the gross position of the TMS electromagnet(s) around the patient's head, as well as the orientation of the face of the magnet. As described in more detail below, the emitted electromagnetic field may be shaped, having regions that are higher intensity surrounded by lower intensity regions. The TMS electromagnet may therefore be oriented so that it is aimed at the target deep brain region.

The positioning and orienting of the TMS electromagnets may be done manually or automatically. Thus, a system for performing TMS may include a gantry, track, arm, or any other positioning device for holding one or more TMS electromagnets. A controller may control one or more drivers for positioning and orienting the TMS electromagnets as described herein.

After positioning, appropriate stimulation to be applied to stimulate the deep brain target region without stimulating (or over-stimulating) intervening regions may be determined. Thus in any of the methods described herein, the appropriate stimulation to be applied by each TMS electromagnet may be determined. In general, the power to be applied by each TMS electromagnet should be limited to prevent undesirable stimulation of non-target regions, particularly regions that are intermediate to the target deep-tissue region and the TMS electromagnet. Thus, in determining the stimulation parameters for each TMS electromagnet, the upper limit may be below the motor threshold level of the intermediate regions. The motor threshold ("MT") refers to the motor threshold for stimulation, a standard (based on stimulation of motor cortex) for evoking a response via Transcranial Magnetic Stimulation; "100% MT" or greater (e.g., "115% MT") may result in an evoked action potential. The stimulation applied may be below threshold (<100% MT), while still summing to provide sufficient (at or above 100% MT) for the deeper brain regions. Thus, the cortical or regions superficial to the deep target may be un-stimulated so that they do not fire action potentials, while still stimulating the deeper region(s).

The power level necessary may depend on the proximity of the TMS electromagnet to the target (distance) as well and the presence and absence of any sulcus or other electrically conductive channel connecting to the target, as well as the number and orientation of the TMS electromagnets. This is illustrated below for FIGS. 5A-6E.

FIGS. 1A and 1B illustrate an array of three (v-shaped) double coils in a configuration designed to stimulate the dorsal cingulate fiber bundles, while leaving the outer cortex relatively undisturbed. The array of TMS electromagnets consists of a set of independently powered coils each aimed at tracts of the anterior cingulate. The coils are oriented in accordance with the dominant fiber activation mode (e.g., horizontal versus transverse), noting that dorsal cingulate fibers run in the sagittal plane, while prefrontal fibers run in the coronal plane. In this configuration, the power is typically assumed to decrease with distance at a fall-off rate that is the same as for a well-characterized 70 mm double coil (i.e., the power is approximately halved for every cm distance). Serially or simultaneously triggered pulses from each coil are delivered at phase-complementary angles. In the case of serial pulses, intervals (e.g., approx. 100 µs), generally within the membrane time constant of the targeted tissue (approx 300 µs for tracts, 4000 µs for cell bodies and axons) are desirable. In the particular configuration shown in FIG. 1A, three (v-shaped) double coils are configured to stimulate the dorsal cingulate fiber bundles, while leaving the outer cortex relatively undisturbed.

The head of the patient 105 is shown transected by plane 110. V-shaped double coil 120 is composed of circular coils 121 and 122, and bent at the center, where the return path of the current in both coils is in the same direction. Similarly, V-shaped double coil 130 is composed of circular coils 131 and 132 joined at a bent center, and V-shaped double coil 140 is composed of circular coils 141 and 142, joined at a bent center. In FIG. 1B, a coronal section is shown where v-shaped double-coil electromagnets 150, 160, and 170 are oriented towards dorsal cingulate target 180 wherein cingulate bundle 190 is a portion of target region 180. In an alternative embodiment, V-shaped coils may be constructed with a "flat bottom", in which each loop is separately bent outward at a point lateral to the medial portion where the loops of each coil is adjacent to that of the other.

Figures 2A, 2B:
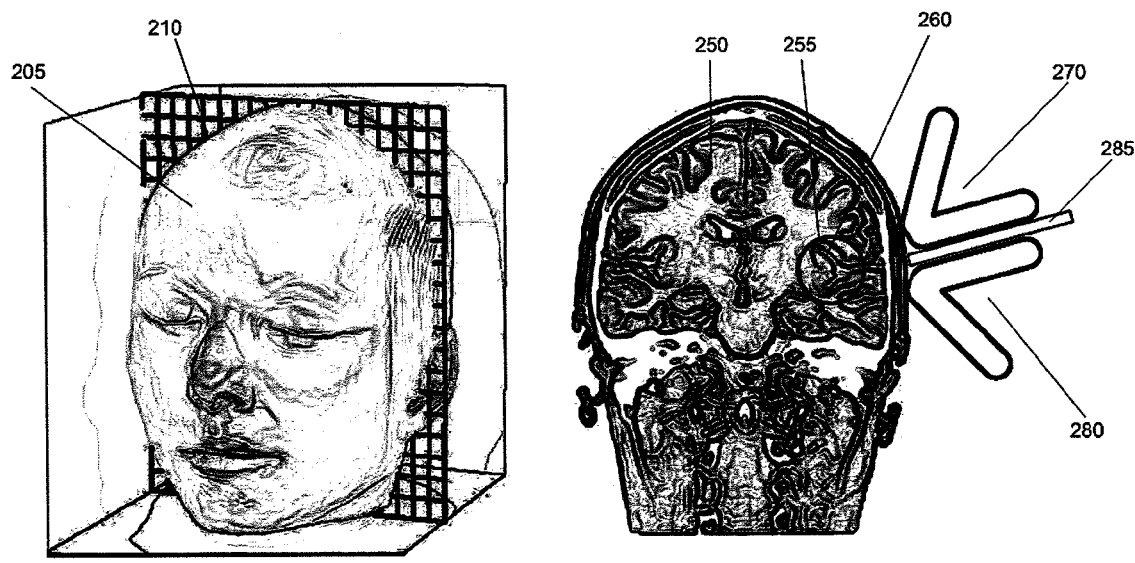
FIGS. 2A and 2B show perspective and partial cross-sectional views, respectively, of an array of two (v-shaped) double coils in a configuration designed to stimulate the insula while leaving the outer cortex relatively undisturbed.

FIG. 2 illustrates an array of two (v-shaped) double coils 270 and 280, in a configuration designed to stimulate insula 260. An image of patient's head 205 is shown in coronal section at plane 210. Brain 250 includes target area 255, chiefly consisting of insula 260. V-shaped coils 270 and 280 are both aimed at target area 255. Shielding 285 may be optionally interposed between coils 270 and 280 to reduce mutual inductance, and may be formed from a high-permeability mu-metal. Shielding may be used with any of the embodiments described herein, and the effect of the shielding may be considered when determining the stimulation parameters. For example, the effect of the mu-metal shielding may alter the power and/or shape of the emitted magnetic field.

Figure 3A:
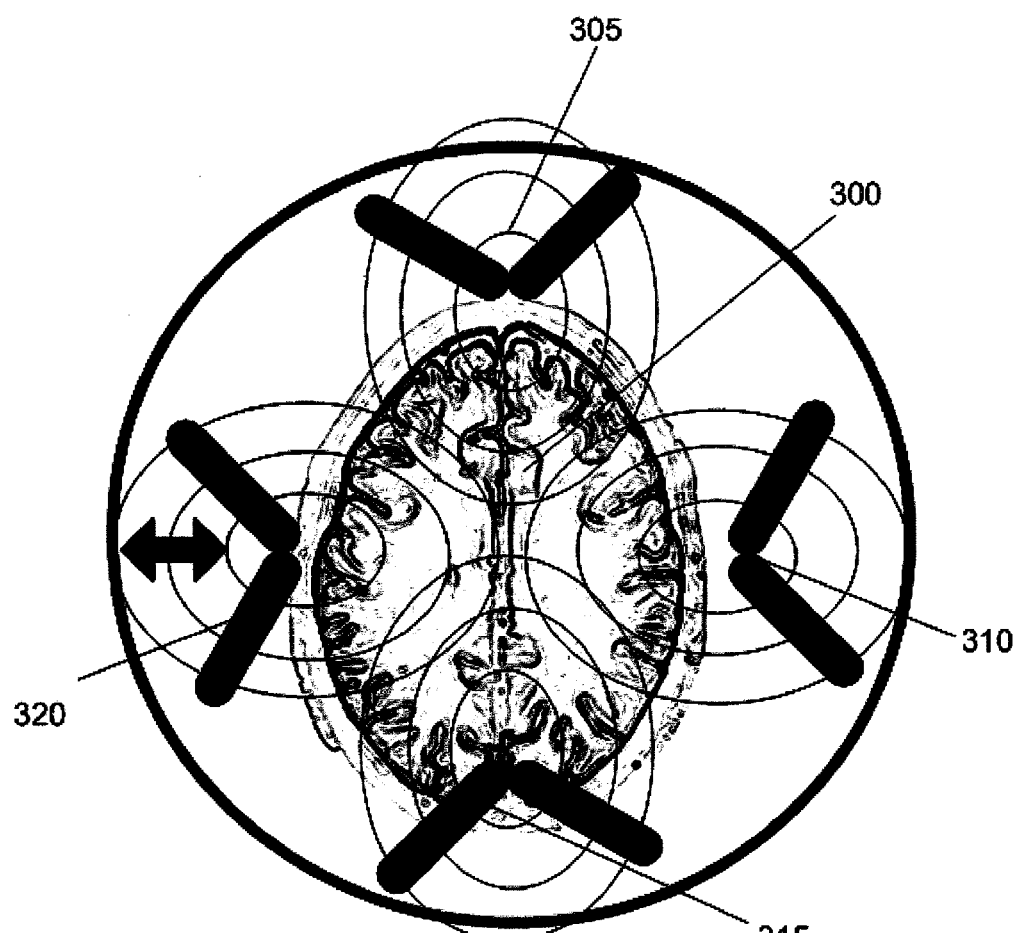
FIGS. 3A and 3B illustrate an array of four (v-shaped) double coils in a mobile configuration designed to stimulate the dorsal cingulate.

FIG. 3A shows an array of four (v-shaped) double coils in a mobile configuration designed to stimulate the dorsal cingulate. In this variation, the electromagnets may be moved either before stimulation (e.g., to focus on a target deep brain region) or they may be moved as part of the therapy. Moving the coils in this manner may allow temporal summation of a target brain region from different stimulation positions relative to the patient. Such a coil-moving device may be like that described in Schneider and Mishelevich U.S. patent application Ser. No. 10/821,807. In the upper portion of the figure, coils 305, 310, 315 and 320 are in locations too distant from the anterior cingulate target 300 to effectively modulate its activity. However, by moving coils into a closer pattern as shown in the lower figure, more effective use of the array becomes possible.

Figure 3B:
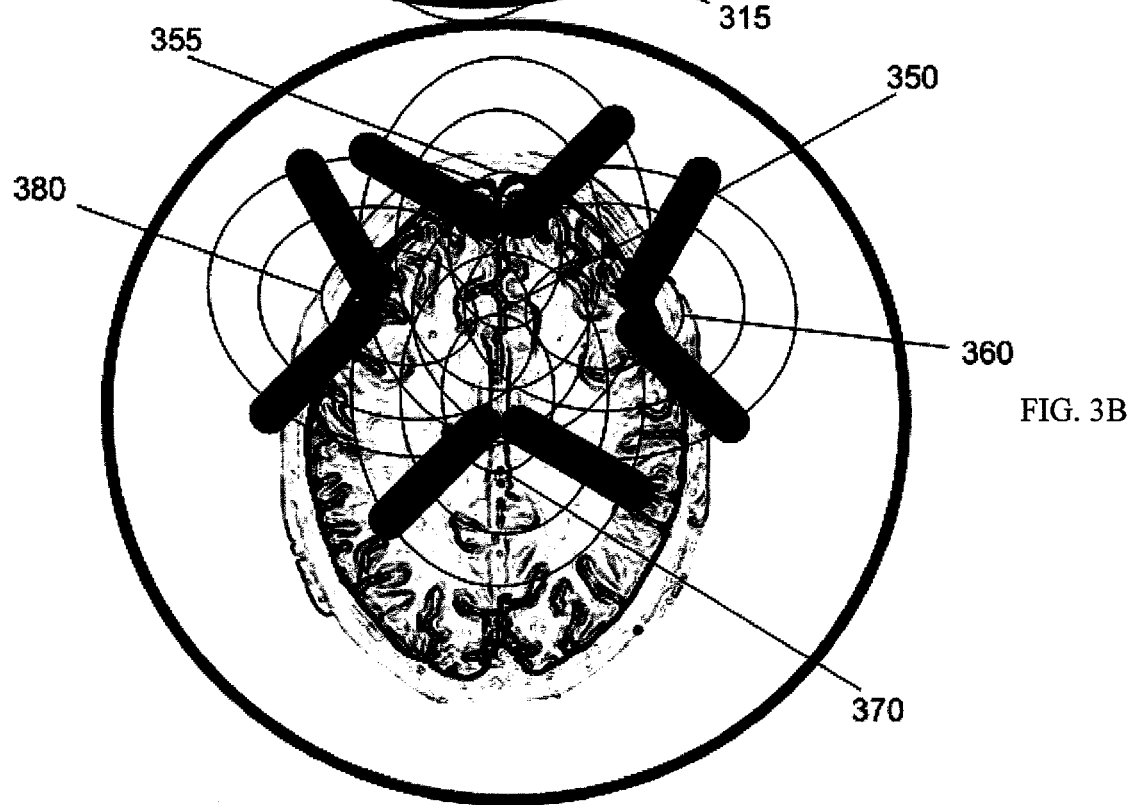

In FIG. 3B, coils 355, 360, 370 and 380 have moved much closer together and closer to dorsal anterior cingulate target 350, in a 3D pattern overlaid upon a 2D axial slice.

Coil Shape

V-Shaped double coils are used in the illustrations herein, although any appropriate TMS electromagnet may be used. These coils are similar to standard double coils, but are bent at the center. Compared with a standard double coil, this configuration provides approximately equal power at the center, but may removes power lateral to the center point to an area more distant from the scalp, resulting in a more focal electric field distribution, and at the same time frees space on the scalp for the placement of additional coils. Even though V-shaped coils are used in these diagrams, it should be understood that other coil designs, for example standard double coils, may also be used instead or in combination. This shape may also maximize the mutual induction of magnetic flux from the central portion of the double coil structure. Examples of such flat-bottomed V-coil design is further described in "FOCUSING MAGNETIC FIELDS WITH ATTRACTOR MAGNETS AND CONCENTRATOR DEVICES" (PCT/US2008/075575) filed Sep. 8, 2008, previously incorporated by reference in its entirety.

Sequential Firing of Coils in Array and Temporal Summation

When multiple magnets are place next to one another, both summation and cancellation affects take place in various spatial locations. One of the difficulties in reaching deep targets with arrays of multiple magnets is the tendency for the field to be pulled toward the periphery, as magnetic fields seek their most efficient course to the opposite polarity. One useful and way of avoiding this "short circuiting" effect is to fire the magnetic pulses sequentially rather than simultaneously. In this manner, magnetic fields may show a more efficacious path toward a target than when fired simultaneously.

For sequentially delivered pulses to have the intended physiological effect, they must be fired in sufficiently rapid sequence to temporally summate. An action potential occurs in a stimulated nerve when a voltage threshold is reached or exceeded. This threshold may be reached over an extended period of time provided that during this time depolarizing forces exceed the repolarizing forces of the cell's ion channels and pumps. Multiple pulses must occur in relatively rapid succession in order to temporally summate. The time during which any two consecutive pulses may summate is sometimes approximated with a figure known as the membrane time constant. In the case of the neocortex, cell bodies and dendrites (gray matter) have a membrane time constant in the neighborhood of 1-10 milliseconds, while mylenated axons of neuronal tracts have membrane constants in the neighborhood of 0.2 to 0.4 milliseconds. Because the measurement of membrane time constants requires intracellular recording (a relatively difficult undertaking), extracellularly measured chronaxie time is sometimes reported as a proxy. Chronaxie time is frequently about 70% of the membrane time constant. However, contrary to common teaching, these pulses need not all occur within a single timeframe dictated by the membrane time constant. Instead, we have found that it is important that the pulsing occur at a rate such that depolarizing forces exceed the repolarizing forces during the period of summation. Accordingly, if a threshold is reached or exceeded sometime within the moving window provided by the balance of polarizing and repolarizing forces, an action potential will result.

In the case of standard rTMS machines (for example, the Magstim Rapid$^2$ units, Magstim Ltd., Wales, UK), each phase of the biphasic pulse complex is approximately 0.1 milliseconds in duration. Thus, if timed and delivered in rapid succession, two to four pulses (for example, generated by two to four different pulse generators) can temporally summate in axons or nerve tracts during a typical membrane time constant. Additionally, more pulses may be summated in a nerve tract, so long as the depolarizing forces build rather than diminish during the course of the delivery. Gray matter (with time constants tenfold greater than white matter) offers the opportunity for the summation of dozens of 0.1 ms pulse phases. The delivery of such closely timed pulses may be achieved by using a plurality of TMS machines, which are triggered in rapid succession when slaved to a controlling computer via their control-interface ports. Alternatively a single machine may include multiple power sources that may be tapped to provide stimulation of the appropriate level to different magnets whose output is coordinated as described herein.

Coil Orientation and Direction of Modulation

The orientation of the stimulation applied (e.g., by an applied magnetic field) may impact the resulting stimulation or inhibition of the target, including deep brain target regions. For example, the double coils shown above may be arranged such that their central long axis is parallel to the fiber bundles of the dorsal aspect of the cingulate. In accordance with standard double coil construction as is known in the art, this means that the direction of the maximal electrical current flow within the coil is parallel to the cingulate fiber bundles. Presuming that the Horizontal Fiber Effect (Barker et al.) holds dominant in this situation, the cingulate bundles will be preferentially activated if the three coils fire in a succession rapid enough to result in summation at the target zone. Alternatively, should the Transverse Fiber Effect (Ruohonen et al.) prove to hold dominant in this situation, then each coil should be rotated 90 degrees such that the induced electric filed is transverse to the cingulate bundles. The methods and systems described herein may be used with either paradigm, and may allow testing to determine (for any given target) which regime to follow, and therefore which orientation to apply.

Downregulation (e.g., suppression) may be achieved by slow or asynchronous pulse rates, for example, 1 Hz or less, applied to a target brain region. At the neuronal circuit level, this effect has been hypothesized to be the result of long-term depression (LTD). Similarly, upregulation augmentation or "stimulation" is frequently achieved using strong rapid pulse rates, for example 5 Hz or greater. At the neuronal circuit level, this effect has been hypothesized to be the result of long-term potentiation (LTP). Intrinsic differences between the properties of various neuronal populations make quite variable the specific parameters required to augment or suppress. In some cases, the parameters required to cause augmentation or suppression are opposite that cited above. The methods described herein may also be tailored to achieve either upregulation or downregulation. For example, some therapeutic targets may include: treatment of depression (e.g., downregulate subgenual cingulate, upregulate dorsal anterior cingulate), treatment of pain (e.g., downregulate dorsal anterior cingulate, down-regulate insula), treatment of obesity (e.g., downregulate orbitofrontal cortex in presence of orexins, upregulate lateral hypothalamic area, downregulate medial hypothalamic area).

Figure 4:
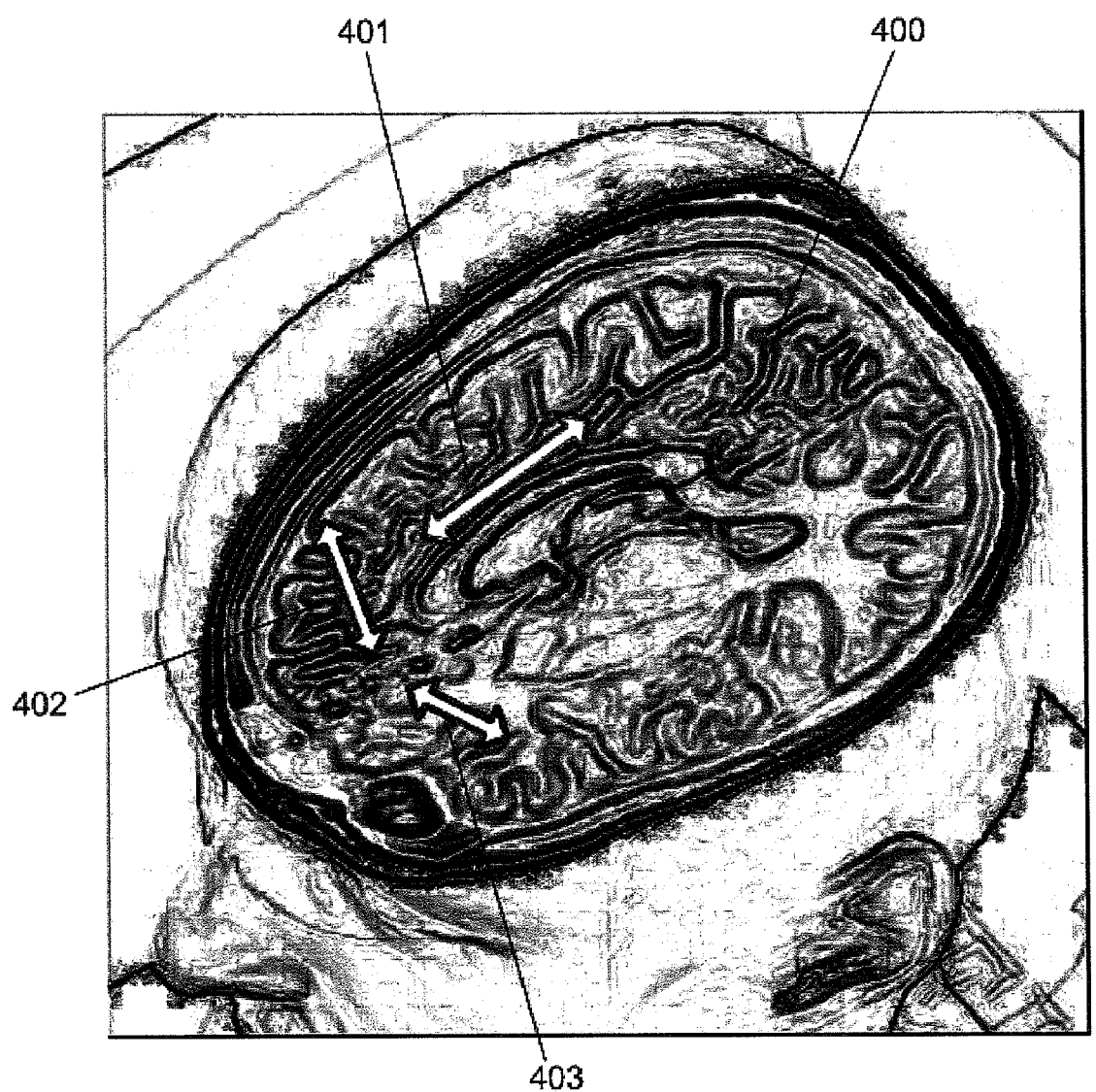
FIG. 4 is a cross-sectional view through a patient's head, showing the contrast between the dorsal cingulate fibers and prefrontal fibers.

FIG. 4 illustrates a biplanar section of a human brain 400, and the contrast between the dorsal cingulate fibers, or cingulate bundle 401 and prefrontal fibers 402 and 403. As can be appreciated from this illustration, dorsal cingulate fibers 401 run predominately in the anterior/posterior direction while prefrontal fibers 402 and 403 predominantly run in the coronal plane.

Benefit of TMS of Sulci to Reach Target: Distance Effects

Figure 5A:
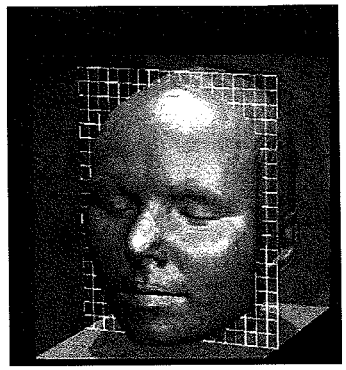
FIGS. 5A-5D and table 5E illustrate a first stimulation scenario, in which the falloff calculation is based on distance from a sulcus to the deep brain target using three trajectories (e.g., 3 TMS electromagnets).
Figure 5B:
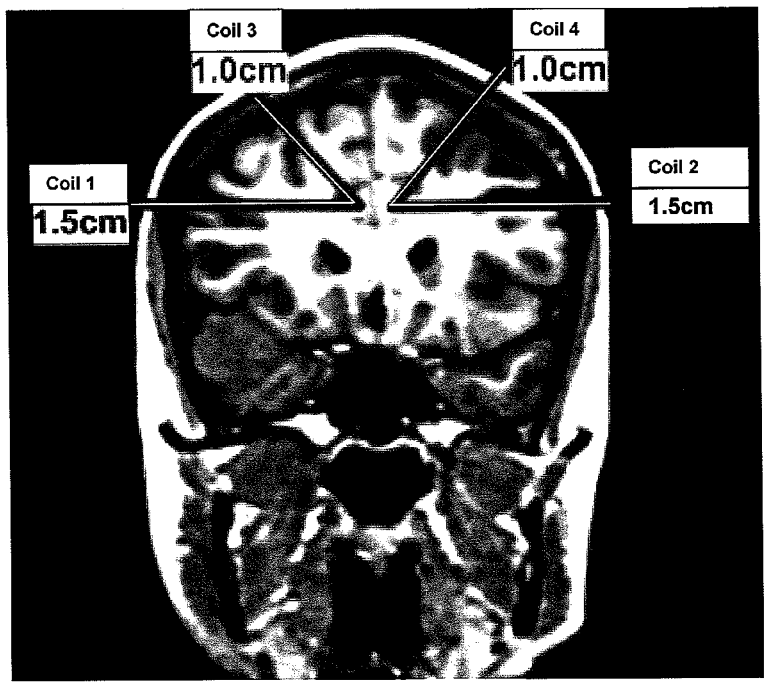
Figure 5C:
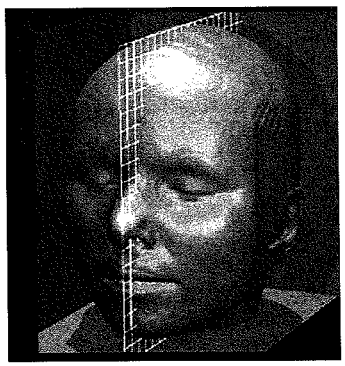
Figure 5D:
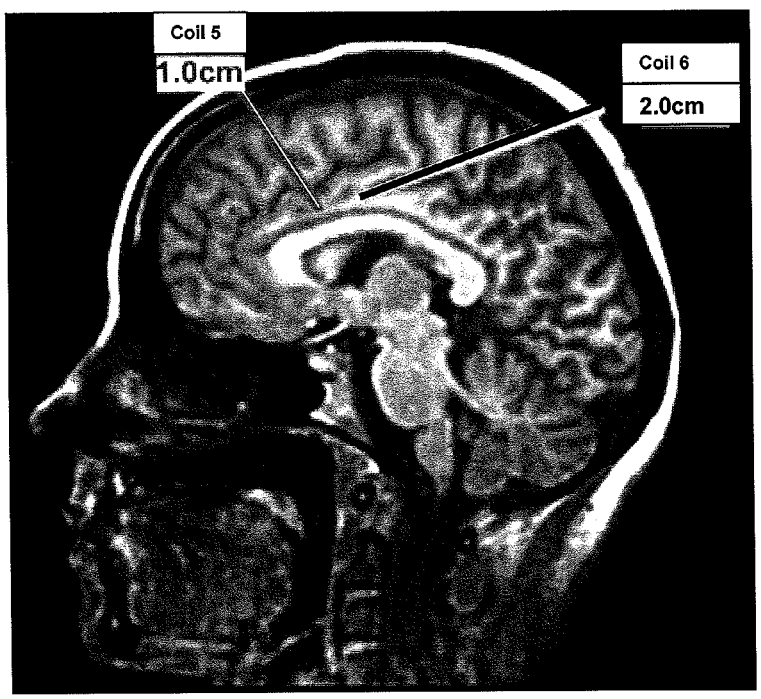
Figure 6A:
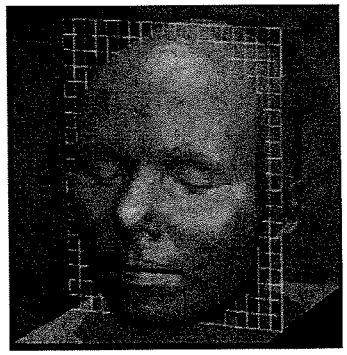
Figure 6B:
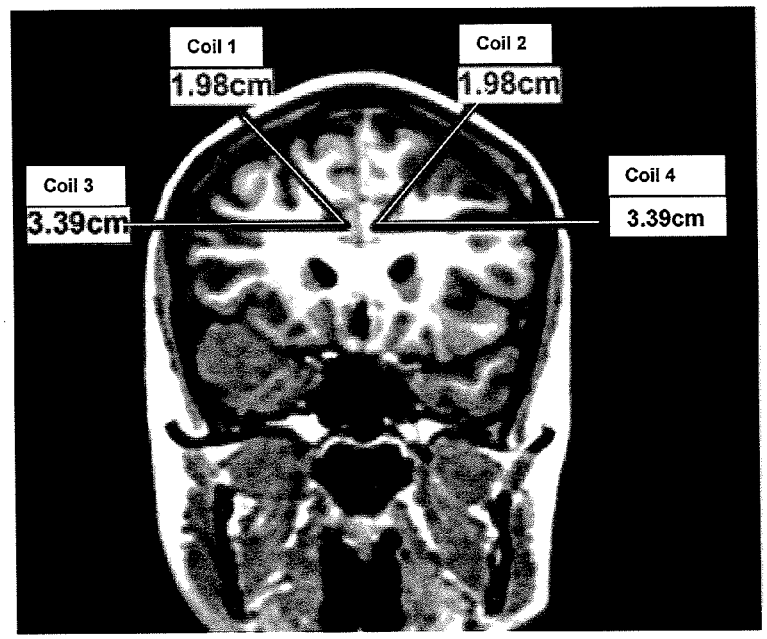
Figure 6C:
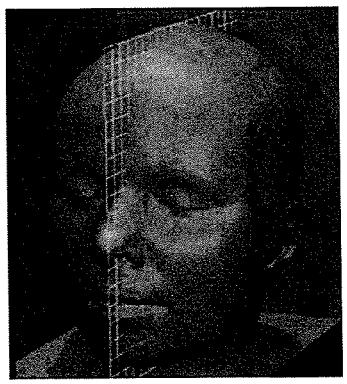
Figure 6D:
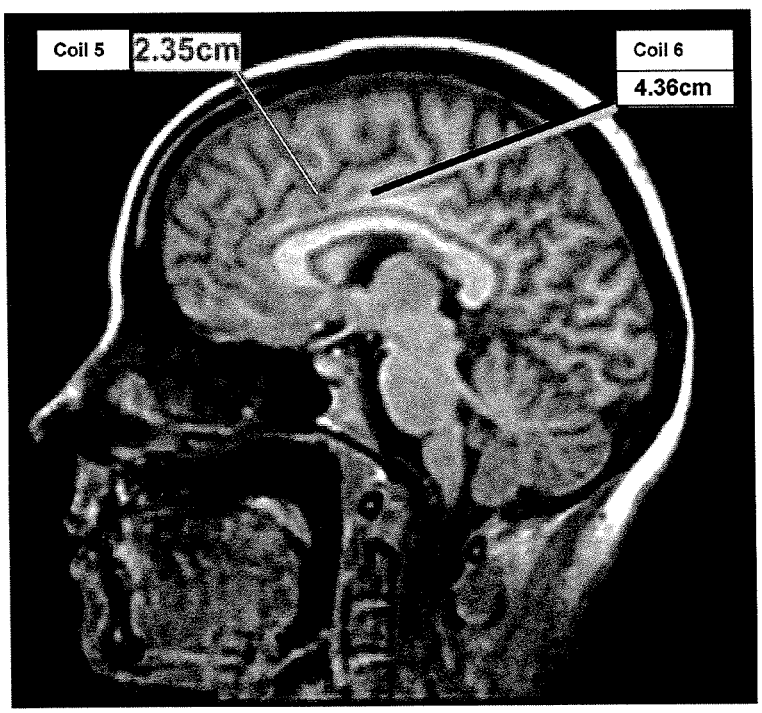

FIGS. 5A-5E and 6A-6E illustrate the use of TMS stimulation using sulci to achieve stimulation of a target deep-brain region. In this example, the deep brain target is the cingulate region. FIGS. 5A-5E illustrates one variation of a method of determining the stimulation parameters using one or more sulci near the deep target region. FIG. 5A illustrates a coronal section taken through a patient's head. The section is illustrated in FIG. 5B, which also shows vectors illustrating the distance from each of four TMS electromagnets located outside of the patient's head to the target cingulate region. FIG. 5b illustrates a midline longitudinal fissure or sulcus that can facilitate the stimulation of the adjacent cingulate structures. In this figure, relatively deep sulci also are oriented towards the target in directions roughly parallel to the lines from the labels Coil 3 and Coil 4. Similarly, FIGS. 5C and 5D show a medial (midsagital) section through the brain, and shows vectors illustrating the distance from two additional TMS electromagnets around the patient's head. In FIGS. 5B and 5D, the coils are labeled as coils 1-6. The brain sections shown in FIGS. 5B and 5D also illustrate various sulci, or regions of sulci that extend adjacent to the target cingulate region. FIGS. 5B and 5D have been labeled to indicate the distance from the target deep brain region (e.g., cingulate region) to the nearest portion of the sulcus through which stimulation from the TMS electromagnet will occur. For example, in FIG. 5B, the second coil (coil 2) on the right, lateral side of the patient's head is oriented so that the electromagnetic field passes through a long region a sulcus running towards the target cingulate region. The distance from the sulcus to the target region may therefore be used to determine a more active falloff estimate for each TMS electromagnet. This more accurate falloff value may be used to determine the power necessary (e.g., minimizing the effect on the non-target tissue by applying only the power necessary at the corrected falloff value), and may also be used to position the TMS electromagnet so that the emitted field will pass through as much of the sulci as possible, to minimize falloff loss. In FIGS. 5B and 5D the distances from the cortical sulcus to the target (cingulate region) are labeled for each TMS electromagnet.

FIG. 5E illustrates the effect of the sulci in determining the power actually seen by the target region. In this example, three of the six TMS electromagnets were simulated as shown in FIGS. 5B and 5D. The total power reaching the target is shown as a percent of MT; each of the three TMS electromagnets was stimulated at less than MT (e.g., 99% MT). Using the 'corrected' distances based on the extend of the sulci through which the magnetic fields will pass, the power reaching the target from each TMS electromagnet was calculated, summing these effects at the target (assuming that the stimulation occurs within the time constant as described above), results in a total power of 116% MT from only three of the six TMS electromagnets.

Thus, in some variations a step of determining a the position and/or stimulation parameter for the TMS system may include optimizing the position of the TMS electromagnet so that the magnetic field passes along or through the longest sulci extent on the way to the target deep brain region. Because the loss of energy in the conductive CSF is much less than in the other neuronal tissue, stimulation through the sulci results in an enhanced effect. The effect of the sulci on stimulation is surprisingly high, as can be seen by comparison to FIG. 6, in which a similar arrangement of TMS electromagnets were calculated without taking into account the effect of sulci.

In FIG. 6A-6D, similar to FIGS. 5A-5D, the positions of six TMS electromagnets oriented around a subject's head and directed at the same target (cingulate region) are shown. Each of the six coils is labeled, and next to each label, the distance from the cortical surface to the target is shown. When the falloff values are calculated using these distances, which do not take into account the approximation of low-loss transmission through the sulci, the resulting calculated power reaching the target from each of the six TMS electromagnets is substantially lower. To illustrate this point, the total power reaching the target from all six TMS electromagnets in this regime is 112% MT, significantly less than the power from only half as many TMS electromagnets shown in FIG. 5A-5E.

Thus, the summation at the target, which may occur in the context of spatial (geometric superimposition) or temporal (network-based) summation, is much less when sulci are not taken into account. Furthermore, by maximizing the projection of the TMS electromagnet field through a sulci, the stimulation parameters can be optimized. As just described, FIG. 5 shows the fall-off calculation based on distance from sulcus to target involving 3 trajectories and subthreshold to minimal surface stimulation. FIG. 6 shows the fall-off calculation based on distance from gyral crown to target involving 5 to 6 trajectories and subthreshold to minimal surface stimulation.

In some variations, it may be beneficial to target the TMS electromagnet to stimulate a deep brain target using the sulci that may connect or extend towards the target. Thus, any of the methods described herein may include a mapping step (e.g., mapping or otherwise determining the trajectory of any sulci near the target), and may also include a step of optimizing the position using the orientations of these sulci. As already described, the power applied (e.g., stimulation protocol) to each TMS electromagnet may also be adjusted based on the presence/absence of the sulci. For example, as illustrate in FIGS. 5A-5E and 6A-6E, the number of TMS electromagnets (as well as which TMS electromagnets to use)

may be determined using the distance from the sulci to the target or the distance from the TMS electromagnet to the target after removing the sulci distance.

REFERENCES

Hemond C, and F. Frengi, "Magnetic Stimulation in Neurology: What We Have Learned from Controlled Studies," In: Neuromodulation: Technology at the Neural Interface. Vol. 10, Number 4, 2007, Blackwell-Synergy Publishers.

Mishelevich D. J. and M. B. Schneider, "Trajectory-Based Transcranial Magnetic Stimulation," U.S. patent application Ser. No. 11/429,504

Mishelevich D. J. and M. B. Schneider, "Focused Magnetic Fields," U.S. Patent Application Ser. No. 60/970,964.

Schneider, M. B. and D. J. Mishelevich, "Robotic Apparatus for Targeting and Producing Deep, Focused Transcranial Magnetic Stimulation," U.S. patent application Ser. No. 10/821,807.

Ueno S, Tashiro T, and K. Harada, "Localized Stimulation of Neural Tissues in the Brain by Means of a Paired Configuration of Time-Varying Magnetic Fields," J. Appl. Phys. 64 (10), 15 Nov. 1988. Pp. 5862-5864.

Agnew et al. Neurosurg, 1987, 20: 143-147.

Bohning et al. Neuroreport. 1997 Jul. 28; 8(11): 2533-2538.

Epstein: J Clin Neurophysiol, Volume 13(3). May 1996: 247-252.

Jalinous R. The New Guide to Magnetic Stimulation. Magstim LTD 2003.

Wassermann, E M. Risk and safety of repetitive transcranial magnetic stimulation: report and suggested guidelines from the International Workshop of the Safety of Repetitive Transcranial Magnetic Stimulation, Jun. 5-7, 1996. Electroencephalography and Clinical Neurophysiology 108 (1998) 1-16.

What is claimed is:

1. A Transcranial Magnetic Stimulation (TMS) method for stimulating a brain region deep within a patient's brain, the method comprising:
   positioning a first TMS electromagnet outside of a patient's head;
   determining the distance between a target deep brain region and a sulcus, wherein the sulcus is within the range of a magnetic field emitted by the first TMS electromagnet;
   determining the direction of a pathway through the sulcus to the target deep brain region;
   determining stimulation parameters for the first TMS electromagnet based on the distance between the target brain region and the sulcus and based on the direction of the pathway through the sulcus to the target deep brain region; and
   applying energy to the first TMS electromagnet at the determined stimulation parameters.

2. The method of claim 1, wherein the step of positioning comprises positioning the TMS electromagnet over the sulcus, wherein the sulcus is adjacent to the target deep brain region.

3. The method of claim 1, wherein the step of positioning comprises aiming the TMS electromagnet at the target deep brain region.

4. The method of claim 1, wherein the step of determining the distance comprises determining the distance between the target deep brain region and a portion of the sulcus closest to the target deep brain region.

5. The method of claim 1, wherein the step of determining the direction of the pathway through the sulcus comprises determining an angle between the pathway through the sulcus and the target deep brain region.

6. The method of claim 1, further comprising aligning the TMS electromagnet based on the direction of the pathway through the sulcus and the angle between the pathway through the sulcus and the target deep brain region.

7. The method of claim 1, wherein the step of determining the stimulation parameters comprises determining the duration, rate and power for the first TMS electromagnet.

8. The method of claim 1, wherein the step of determining the stimulation parameters comprises estimating the power achieved at the target based on estimating the attenuation of the applied power using the distance from the target deep brain region and the sulcus.

9. The method of claim 1, further comprising positioning a second TMS electromagnet outside of the patient's head.

10. The method of claim 9, further comprising determining stimulation parameters for the second TMS electromagnet based on the distance between the target brain region and a sulcus that is within the range of a magnetic field emitted by the second TMS electromagnet.

11. The method of claim 10, further comprising determining the direction of the pathway to the target deep brain region through the sulcus that is within the range of a magnetic field emitted by the second TMS electromagnet, and further wherein the step of determining the stimulation parameters for the second TMS electromagnet comprises determining the stimulation parameters based on the direction of the pathway to the target deep brain region through the sulcus that is within the range of a magnetic field emitted by the second TMS electromagnet.

12. The method of claim 11, wherein the step of determining the direction of the pathway to the target deep brain region through the sulcus that is within the range of a magnetic field emitted by the second TMS electromagnet comprises determining an angle between the pathway through the sulcus that is within range of the magnetic field emitted by the second TMS electromagnet and the target deep brain region.

13. The method of claim 11, further comprising aligning the second TMS electromagnet based on the direction of the pathway through the sulcus that is within the range of a magnetic field emitted by the second TMS electromagnet and the angle between the pathway through the target deep brain region and the sulcus that is within the range of a magnetic field emitted by the second TMS electromagnet.

14. The method of claim 10, wherein the step of determining the stimulation parameters comprises limiting the power for each TMS electromagnet to be below the motor threshold at the cortical surface.

15. A Transcranial Magnetic Stimulation (TMS) method for stimulating a brain region deep within a patient's brain, the method comprising:
   positioning a plurality of TMS electromagnets outside of a patient's head;
   aligning the plurality of TMS electromagnets so that the direction of the maximal current flow within the TMS electromagnets is aligned with a fiber bundle of a target deep brain region;
   determining stimulation parameters for each TMS electromagnet so that the target deep brain region is stimulated by activation of the TMS electromagnets more than non-target cortical surface regions; and
   applying energy to each of the plurality of TMS electromagnets at the determined stimulation parameters.

16. The method of claim 15, wherein the step of determining the stimulation parameters comprises limiting the power for each TMS electromagnet to be below the motor threshold at the cortical surface.

17. A Transcranial Magnetic Stimulation (TMS) method for stimulating a cingulate region of a patient's brain while leaving the outer cortex relatively undisturbed, the method comprising:
- aiming a plurality of independently powerable TMS electromagnets at the cingulate region tracts of the patient's brain;
- determining stimulation parameters for each TMS electromagnet so that the power of the field emitted by each TMS electromagnet at the cortical surface is below the motor threshold; and
- triggering pulses from the TMS electromagnets at phase-complementary angles, wherein pulses from two or more TMS electromagnets are triggered within a membrane time constant of the target cingulate region.

18. The method of claim 17, wherein the step of aiming comprises aiming the plurality of independently powerable TMS electromagnets at tracts of the cingulate region.

19. The method of claim 17 wherein the step of aiming comprises aiming the plurality of independently powerable TMS electromagnets at tracts of the patient's anterior cingulate.

20. The method of claim 17, wherein the step of aiming comprises orienting each of the TMS electromagnets to stimulate the tracts of the cingulate region horizontally.

21. The method of claim 17, wherein the step of aiming comprises orienting each of the TMS electromagnets to stimulate the tracts of the cingulate region transversely.

22. The method of claim 17, wherein the step of aiming comprises aiming a plurality of independently powerable V-shaped TMS electromagnets.

23. The method of claim 17, wherein the step of triggering pulses comprises simultaneously triggering pulses from the two or more TMS electromagnets.

24. The method of claim 17, wherein the step of triggering pulses comprises triggering pulses from two or more TMS electromagnets within about 300 μs.

25. A Transcranial Magnetic Stimulation (TMS) method for stimulating an insula region of a patient's brain while leaving the outer cortex relatively undisturbed, the method comprising:
- positioning a plurality of independently powerable TMS electromagnets outside of the patient's head;
- aiming the plurality of independently powerable TMS electromagnets at the insula region of the patient's brain;
- determining stimulation parameters for each TMS electromagnet so that the power of the field emitted by each TMS electromagnet at the cortical surface is below the motor threshold; and
- triggering pulses from the TMS electromagnets at phase-complementary angles, wherein pulses from two or more TMS electromagnets are triggered within the membrane time constant of the target insula region.

26. The method of claim 25, further comprising shielding the plurality of independently powerable TMS electromagnets to prevent mutual inductance.

27. The method of claim 26, wherein the step of shielding comprises shielding with a high-permeability mu-metal.

28. The method of claim 25, wherein the step of aiming comprises aiming a plurality of independently powerable V-shaped TMS electromagnets.

29. The method of claim 25, wherein the step of triggering pulses comprises simultaneously triggering pulses from the two or more TMS electromagnets.

30. The method of claim 25, further comprising moving one or more of the TMS electromagnets and triggering additional pulses from the TMS electromagnets.

31. A Transcranial Magnetic Stimulation (TMS) method for stimulating a cingulate region of a patient's brain while leaving the outer cortex relatively undisturbed, the method comprising:
- aiming a plurality of independently powerable TMS electromagnets at the cingulate region tracts of the patient's brain;
- determining stimulation parameters for each TMS electromagnet so that stimulation at the target deep brain region from the plurality of TMS electromagnets is greater than the stimulation at a cortical surface; and
- triggering pulses from the TMS electromagnets at phase-complementary angles, wherein pulses from two or more TMS electromagnets are triggered within a membrane time constant of the target cingulate region.

32. A Transcranial Magnetic Stimulation (TMS) method for stimulating a brain region deep within a patient's brain, the method comprising:
- positioning a plurality of TMS electromagnets outside of a patient's head;
- aligning the plurality of TMS electromagnets with a direction of a fiber bundle of a target deep brain region;
- determining stimulation parameters for each TMS electromagnet so that stimulation at the target deep brain region from the plurality of TMS electromagnets is greater than the stimulation at a cortical surface due to a magnetic field emitted by each TMS electromagnet; and
- applying energy to each of the plurality of TMS electromagnets at the determined stimulation parameters.

* * * * *